United States Patent

Schmidinger et al.

[11] Patent Number: 6,152,736
[45] Date of Patent: Nov. 28, 2000

[54] DENTAL TURBINE

[76] Inventors: Fränk Schmidinger, Rosenheimer Strasse 6a, Töging, 84513, Germany; Herbert L. Biebl, Neuöttinger Strasse 38, Altötting, 84503, Germany

[21] Appl. No.: 09/319,549

[22] PCT Filed: Nov. 10, 1997

[86] PCT No.: PCT/EP97/06244

§ 371 Date: Aug. 9, 1999

§ 102(e) Date: Aug. 9, 1999

[87] PCT Pub. No.: WO98/24382

PCT Pub. Date: Jun. 11, 1998

[30] Foreign Application Priority Data

Dec. 6, 1996 [DE] Germany .............. 196 50 748

[51] Int. Cl.[7] .............. A61C 1/05; F01D 15/06
[52] U.S. Cl. .............. 433/132; 415/904
[58] Field of Search .............. 433/125, 131, 433/132; 415/904

[56] References Cited

U.S. PATENT DOCUMENTS

| 3,141,650 | 7/1964 | Saffir .............. 433/132 |
| 3,147,951 | 9/1964 | Cain, Jr. et al. .............. 415/904 |
| 3,786,875 | 1/1974 | Merle .............. 415/904 |
| 4,203,222 | 5/1980 | Mattchen .............. 433/129 |

FOREIGN PATENT DOCUMENTS 433394   9/1967   Switzerland .

*Primary Examiner*—Ralph A. Lewis
*Attorney, Agent, or Firm*—Townsend and Townsend and Crew LLP

[57] ABSTRACT

A dental turbine comprises a rotor (10) which is rotatably accommodated in a housing (12), the housing (12) having an outlet opening (23) for propellant air which causes the rotor (10) to rotate. The rotor (10) comprises a flow duct whose outlet opening (36) imposes a tangential component on the outflowing propellant air.

6 Claims, 2 Drawing Sheets

DENTAL TURBINE

FIELD OF THE INVENTION

The present invention relates to a dental turbine. Such dental turbines are basically known and have a bladed wheel as a rotor, onto which propellant air emerging from the outlet opening flows tangentially. In this way the rotor is made to rotate and drives a drill bit which can be secured to the rotor.

DISCUSSION OF THE PRIOR ART

In the known dental turbines which are operated with a supply pressure of about 5 bar and have a speed of rotation of the order of magnitude of 250,000 rpm, the generally known noise of the dentist's drill arises in operation, which—as a result of its high intensity and its frequency—can be heard even through closed doors. This noise not only disturbs the patients treated and the patients in the waiting room but can also cause hearing damage to the dentists, since they are exposed to this noise daily. As a remedy it has already been suggested that ear protection should be worn during the treatment.

Since the blades of the rotor are loaded tangentially by compressed air in the known dental turbines, a transverse force arises when the dental turbine is switched on and is disturbing for the dentist carrying out the treatment, because the drill is displaced sideways by it. Accordingly, it would be desirable if the drill were not to exhibit any displacement which has to be compensated for by the dentist.

In the known apparatus it is furthermore disadvantageous that on interruption of the propellant air within the turbine housing, a reverse suction effect occurs, since the rotor, which continues to run, generates a vacuum as a result of the switched off propellant air, whereby aerosols which contain bacteria and the like can be sucked out of the oral cavity of the patient into the rotor housing. On subsequent switching on again of the propellant air, the aerosol components are conveyed out of the turbine space again, which is unhygienic and involves the danger of transfer of pathogens when patients change. In order to avoid these effects, various solutions have been proposed in the prior art; however, these were always complicated design-wise.

SUMMARY OF THE INVENTION

It is the problem (object) underlying the invention to provided a dental turbine which overcomes the above described problems.

This object is satisfied in particular in that the rotor has a flow passage, the outlet opening of which imposes a tangential component on the outflowing propellant air. In this way the rotor does not rotate with the flow which impinges on it but rather a reaction is generated within the flow passage which sets the rotor rotating. At the same time, the spacing between the outlet opening and the surface of the rotor onto which flow takes place remains substantially constant during a rotation and the surface of the rotor, on which the flow impinges, does not undergo any change in shape.

It has namely been found that the disturbing whistling noise in the operation of customary dental turbines is not produced by the bearings or the like but is rather produced by the propellant air at the outer periphery of the rotor been "chopped" by the individual blades. Since a new turbine blade continually enters into the propellant air stream in customary rotors, the shape of the surface, on which the flow impinges, continuously changes as does the spacing of the surface, on which the flow impinges, from the outlet opening. Through the design of the rotor in accordance with the invention it is, however, ensured that even with a rotation of the rotor the outflowing propellant air always encounters a constant surface at a constant spacing from the outflow opening, whereby the disturbing noise is fully removed.

Advantageous embodiments of the invention are described in the description, in the drawings, and also in the subordinate claims.

In accordance with an advantageous embodiment of the invention, the outlet opening can be arranged substantially concentric to the axis of rotation of the rotor. In this embodiment the additional advantage results that on loading of the rotor with propellant air, any form of transverse force which could cause a displacement of the drill tool is removed. Provided the cross-sectional area of the outlet opening extends perpendicular to the axis of rotation, a particularly good coupling results.

In accordance with a further embodiment of the invention, a return can be provided in the housing for the return flow of the propellant air and preferably communicates with a ring-like collecting channel. A collecting channel of this kind favors the return flow of the air emerging from the rotor and the collection of this air in the direction of the return.

In accordance with a further advantageous embodiment of the invention, the flow passage is closed at its four sides. In contrast to the rotors known from the prior art, which are provided with blades or the like at their periphery, the flow passage provided in this embodiment enables a generation of the reaction effect in the interior of the rotor. This further contributes to preventing a disturbing development of noise.

It is particularly advantageous when the flow passage has a substantially centrally arranged axial inlet. In this way no transverse force arises with flow onto the rotor, and thus also no lateral displacement of the drill.

The outlet opening of the flow passage can be arranged at the outer periphery of the rotor. In this embodiment particularly favorable flow conditions are present, since the propellant air which emerges at the outer periphery of the rotor can be favorably collected and returned.

In accordance with a further embodiment, the flow passage has an inlet and a plurality of outlet openings, which are preferably symmetrically arranged. In this way a particularly steady operation of the dental turbine is achieved and balancing of the rotor can be dispensed with. In this respect it is particularly advantageous when the flow passage has a radially extending part, since in this way the propellant air is led to the outlet point on the shortest path.

In accordance with a further advantageous embodiment of the invention the flow passage has a part which extends substantially in the circumferential direction of the rotor, which preferably converges with the outer periphery of the rotor. In this way particularly favorable flow conditions are provided, since the air which emerges from the rotor is not compressed between the rotor and the housing, but can rather expand in the converging part passage.

It is particularly advantageous when the flow passage deflects the flow guided therein at the outer rim of the rotor, since then the largest possible torque is achieved. It is also advantageous to provide a decompression space at the outlet side end of the flow passage in order to keep down the frictional losses through the air emerging from the rotor and expanding.

Since the disturbing whistling noise has been completely removed by the dental turbine of the invention, it can be advantageous to also improve the journalling of the rotor in order to further reduce the bearing noises that are present. For this purpose at least one bearing of the rotor can be formed as a tandem bearing, which preferably has two bearings, with the outer ring of the one bearing been coupled to the inner ring of the other bearing. In this way the rolling speed is halved and thus the noise generated by the bearing is also reduced by half.

The dental turbine of the invention is characterized in that the disturbing whistling noise is fully removed. Furthermore, no disturbing transverse force is produced on switching on the dental turbine, so that the drill can already be precisely positioned prior to switching on. Finally, with the dental turbine of the invention, no aerosols and/or bacteria are sucked into the turbine space on switching off the propellant air, because—in contrast to the known rotors—the rotor of the invention does not act as an impeller wheel pump when running down and centrifuge the air present in the rotor chamber radially outwardly into the return passage. Accordingly, no vacuum arises in the region of the rotor shaft, which could have the consequence of a flow of air from the outside through the existing bearing gaps or the like.

BRIEF DESCRIPTION OF THE DRAWINGS

In the following the present invention will be described purely by way of example with reference to advantageous embodiments and to the accompanying drawings, in which are shown.

DETAILED DESCRIPTION OF PREFERRED EMBODIMENTS

Figure 1:
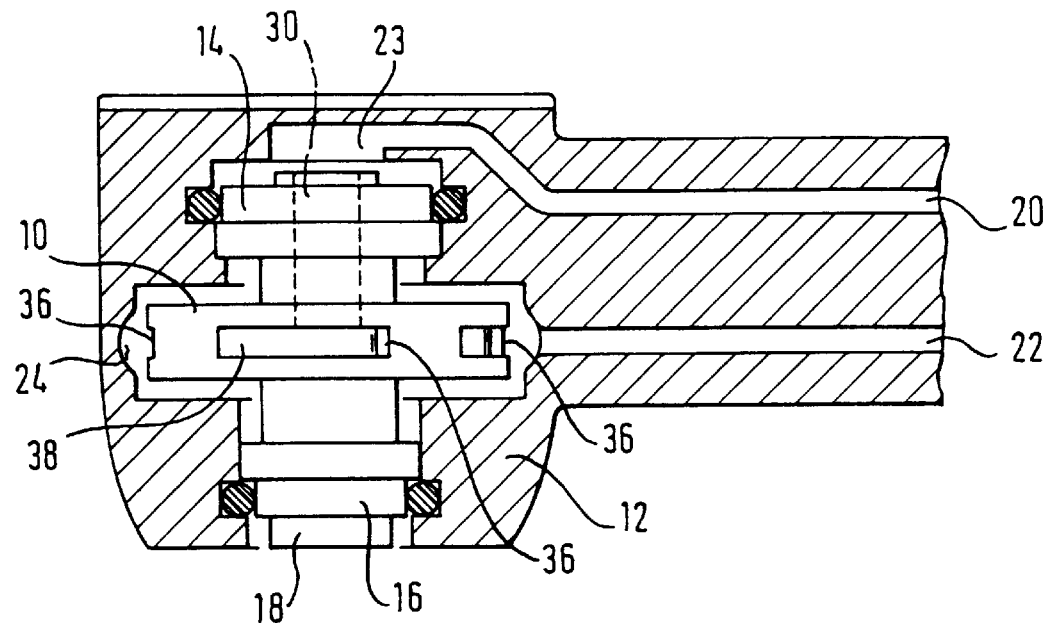
FIG. 1 a cross-section through a dental turbine in accordance with the invention.

The dental turbine shown in FIG. 1 has a rotor 10, which is received in a housing 12, formed as the handle of a dentist's drill. The rotor 10 is rotatably held in the housing 12 by two only schematically indicated bearings 14 and 16, which are respectively received in the housing 12 and each sealed via an O-ring. A drill bit or the like can be inserted into the lower end of the rotary shaft 18 in the customary manner.

In the housing 12 there are provided a feed passage 20 and a return passage 22, through which the pressurized propellant air flows in and away. The feed passage 20, which extends through the handle of the drill, opens into an outlet opening 23, which is disposed axially and concentrically to the axis of rotation of the rotor 10. The return passage 22 for return flowing propellant air communicates in the region of the rotor housing with a ring-like collecting passage 24, which surrounds the rotor 10 at its outer periphery. Furthermore, non-illustrated supplies for spray water and light are provided in the housing.

The rotor 10 of the dental turbine has a flow passage having a centrally arranged axial inlet 30, which opens axially outwardly in the direction of the outlet opening 23 and which is shown in broken lines in FIG. 1. The downstream end of the axial inlet 30 communicates with a centrally disposed distributor section 32 (FIG. 2) which is adjoined by four radially extending part passages 34 arranged at uniform angular intervals.

Figure 2:
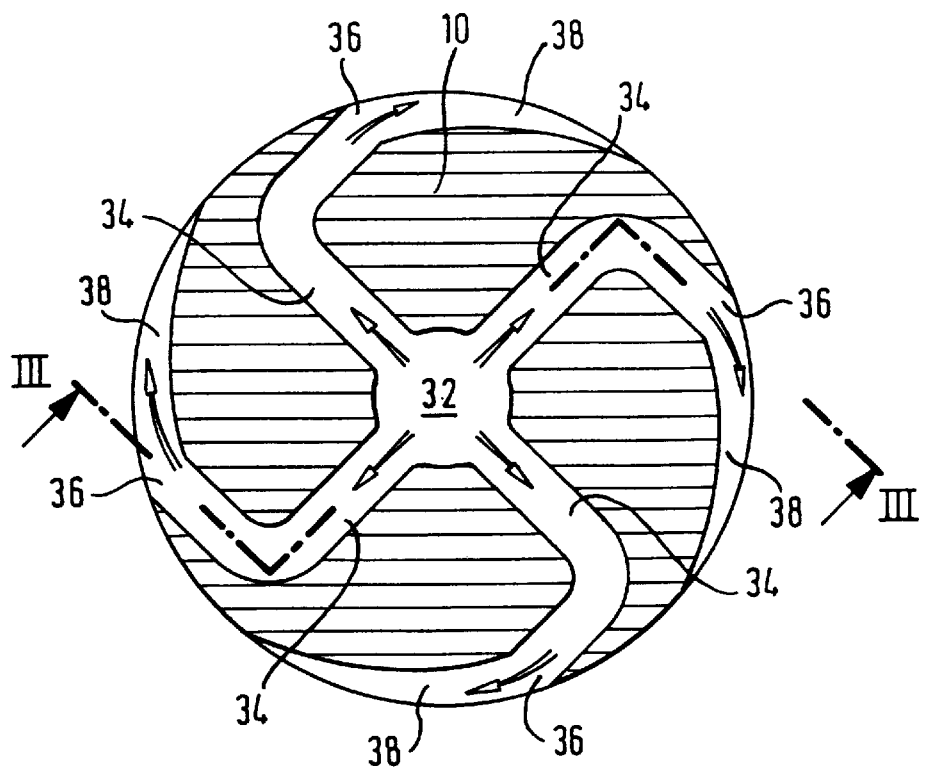
FIG. 2 an enlarged cross-sectional view of the rotor of FIG. 1.

As FIG. 2 shows, the part passages 34 are each curved in the clock-wise sense, i.e. in the same sense by ca. 90° at the outer rim of the rotor 10 and followed in each case by an outlet opening 36. The outlet opening 36 are located at the outer periphery of the rotor 10 and impart a tangential component to the outflowing propellant air.

In the region of the outlet opening 36, the outlet of each part flow passage has a part passage 38 which extends in the peripheral direction of the rotor 10 and converges with the outer periphery of the rotor. In this way a decompression space is provided at the outlet side end of each part flow passage, which opens towards the outer periphery of the rotor and has a scythe-like shape when seen in cross-section.

On taking the above described drill into operation, propellant air, which can have a pressure in the range from about 5 to 10 bar, is supplied through the feed passage 20, whereby it flows out of the outlet opening 23 of the housing 12 in the direction of the rotor axis. The outflowing air subsequently passes through the axial inlet 30 of the rotor 10 and from there into the distributor section 32. From there the air flows through the part passages 34 and is distributed cross-wise and in each case deflected into the radial direction. In the region of the deflections provided at the outer rim of the rotor 10, each part flow is deflected through 90°, and subsequently flows through the outlet opening 36 out of the rotor. In this way a reaction is exerted on the rotor 10 at four points arranged symmetrically over the periphery so that the rotor turns (in FIG. 2 in the counterclockwise sense). In the region of the outlet opening 36 the outflowing propellant air in each case finds a decompression space 38, which enables a gentle expansion. The propellant air which has flowed through the rotor is collected in the ring-like collecting passage 24 and flows back through the return passage 22.

On switching off the dental turbine the feed of the pressurized propellant air is stopped, whereby the rotor 10 runs down. During this, however, no air is sucked through the lower bearing 16 of the rotor and also no aerosol is sucked into the housing, since the rotor of the invention does not produce any sucking conveying action. Also no disturbing jerk arises on switching on the dental turbine, since the torque acting on the rotor is completely uniformly and symmetrically distributed over the rotor.

Figure 3:
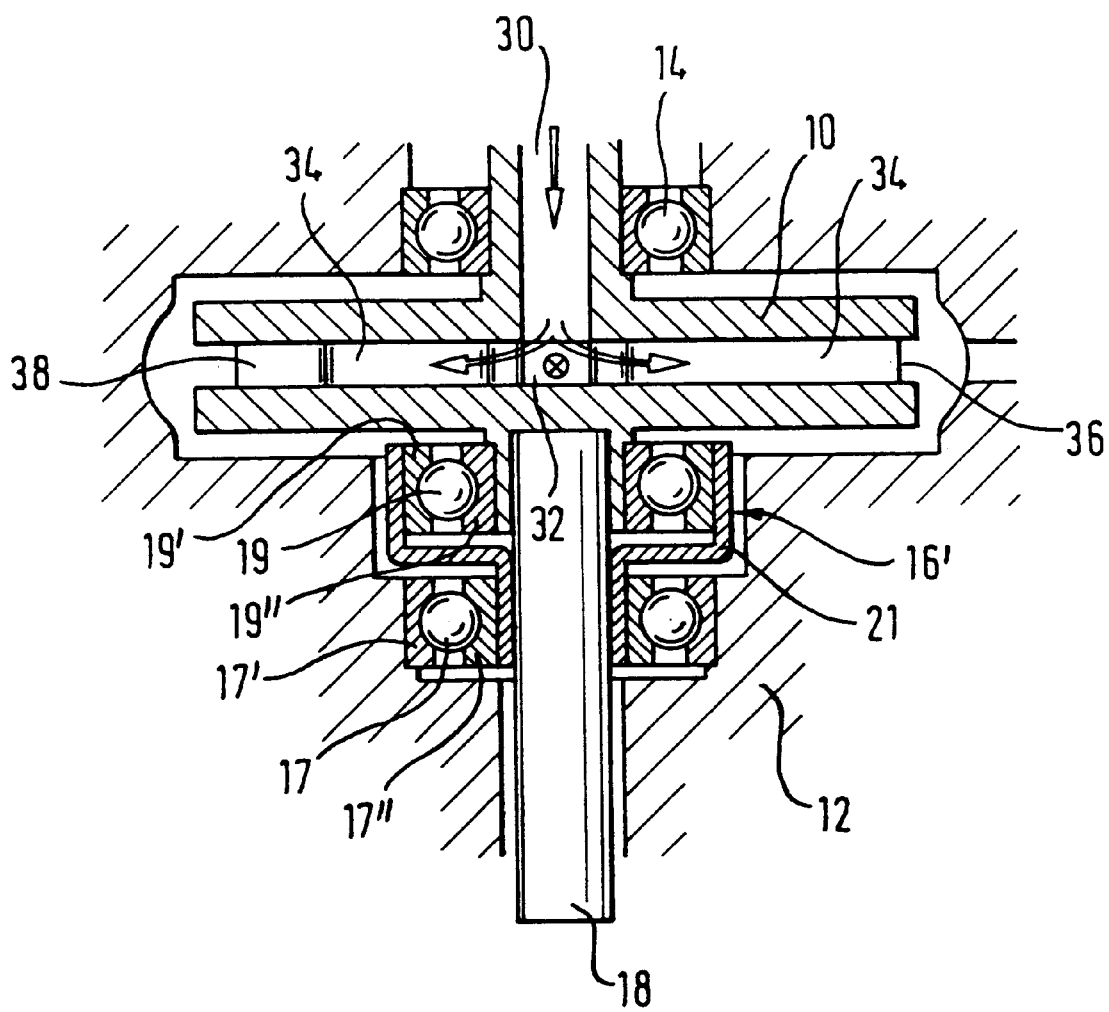
FIG. 3 a schematic cross-sectional view of a tandem bearing, with the rotor being sectioned along the line III—III of FIG. 2.

FIG. 3 shows a further embodiment of a lower bearing which is formed as a tandem bearing 16'. The tandem bearing 16' includes two coupled bearings 17 and 19, with the outer ring 19' of the upper bearing in FIG. 3 being firmly connected via a coupling ring 21 to the inner ring 17" of the lower bearing 17 in FIG. 3. The outer ring 17' of the lower bearing is connected to the housing 12. The inner ring 19" of the upper bearing 19 guides the shaft 18 of the rotor 10. Through the coupling ring 21 of cup-like shape, a fixed connection is produced between the two bearings, and at the same time restrains any possible tilting moment. Through this bearing the rolling speed is halved and the bearing noise which arises is also reduced by half. Naturally, both bearings 14 and 16 of the rotor can be formed as a tandem bearing. It is also possible to form the bearings as radial bearings or as horizontal bearings. The upper bearing 14 can also have a seal, for example a labyrinth seal, in order to prevent the inflowing propellant air flowing through the bearing and not through the axial inlet 30.

The dental turbine of the invention is characterized by its smooth running, its jerk-free start and its easy serviceability. Since the rotor can be made axially very narrow in comparison to customary rotors, the constructional height of the dental turbine as a whole can be reduced in the region of its headpiece, which in particular brings advantages when treating children.

What is claimed is:

1. Dental turbine comprising a rotor (10) which is rotatably received in a housing (12) having an inlet opening (23) for propellant air, a receiving space for the rotor (10) and a propellant air outlet (22), wherein the rotor can be loaded with propulsion air via an axial inlet and has substantially radially extending flow passages extending to the outer periphery and having tangential outlets, via which the outflowing propellant air produces tangential drive components which make the rotor rotate, characterized in that the rotor (10) is of disk-like shape; in that the rotor (10) is axially non-displaceably journalled in the housing (12) by means of mechanical bearings (14, 16); in that the rotor (10) has a co-rotating, journalled, axial inlet part (30) to the propellant air feed extending to the inlet opening (23); in that the substantially radially extending flow passages provided in the rotor (10) each merge into a part (36) extending substantially in the circumferential direction of the rotor (10) and continuing the radial flow passage (34); in that the rotor (10) is surrounded by a ring-like collection channel (24) formed in the housing and into which the rotor flow passages (34, 36) open via decompression spaces (38) formed in the rotor (10) and in that the decompression spaces (38) have a scythe-like shape in cross-section.

2. Dental turbine in accordance with claim 1, characterized in that the inlet opening (23) is arranged substantially concentrically to the axis of rotation of the rotor (10), with the cross-sectional surface of the inlet opening (23) extending perpendicular to the axis of rotation.

3. Dental turbine in accordance with claim 1, characterized in that the ring-like collection channel (24) is connected to a return (22) for propellant air which is flowing back.

4. Dental turbine in accordance with claim 1, characterized in that a centrally disposed distributor section (32) is associated with the flow passages.

5. Dental turbine in accordance with claim 1, characterized in that at least one bearing of the rotor (10) is formed as a tandem bearing (16').

6. Dental turbine in accordance with claim 5 characterized in that the tandem bearing (16') has two bearings (17, 19), with the outer ring (19') of the one bearing (19) being coupled to the inner ring (17") of the other bearing (17).

* * * * *